US007141245B2

(12) United States Patent
Das

(10) Patent No.: US 7,141,245 B2
(45) Date of Patent: Nov. 28, 2006

(54) PROCESS FOR PREPARATION OF A MICROBIAL AGENT

(75) Inventor: Bina Pina Das, Delhi (IN)

(73) Assignee: National Institute of Communicable Diseases, Delhi (IN)

( * ) Notice: Subject to any disclaimer, the term of this patent is extended or adjusted under 35 U.S.C. 154(b) by 162 days.

(21) Appl. No.: 10/468,908

(22) PCT Filed: Dec. 26, 2001

(86) PCT No.: PCT/IN01/00226

§ 371 (c)(1),
(2), (4) Date: Aug. 26, 2003

(87) PCT Pub. No.: WO03/013238

PCT Pub. Date: Feb. 20, 2003

(65) Prior Publication Data

US 2004/0219692 A1 Nov. 4, 2004

(30) Foreign Application Priority Data

Aug. 8, 2001 (IN) .............................. 833/DEL/01

(51) Int. Cl.
*A61K 39/002* (2006.01)
(52) U.S. Cl. ............................. 424/269.1; 424/265.1; 435/243; 435/258.1
(58) Field of Classification Search ............. 424/269.1, 424/258.1, 265.1; 435/258.1, 243
See application file for complete search history.

(56) References Cited

OTHER PUBLICATIONS

Das, Bina Pina. Current Science, Aug. 2003. 85(4): 483-489. * Abstract only at this time.*
Struder-Kypke Michaela. Nov. 1999. Limnolgica. 29(4): 407-424. *Abstract only at this time.*
Norton et al (Journal of Invertebrate Pathology. 1992. vol. 60(2): 164-170) *Abstract only at this time.*

* cited by examiner

*Primary Examiner*—Jennifer E. Graser
(74) *Attorney, Agent, or Firm*—Venable LLP; Catherine M. Voorhees; Kavita B. Lepping

(57) ABSTRACT

A method of killing mosquito larvae and particularly the species comprising *Culex tritaeniorhynchus, Cx. pseudovishnui, Cx. (Cx)* sp., *Cx. (Lutzia)* sp. and *Anopheles hyrcanus* group which comprises in allowing *Chilodonella uncinata* as a ciliated protozoa to be present in said host larvae, allowing the ciliated protozoa to form a hole in the wall of the larvae and to enter into the haemocoelomic cavity of the larvae and to thereby allow the ciliate to feed on the host larvae and simultaneously allowing the host larvae to grow and allow a multiplication of the ciliate, and whereby the multiplied ciliates kill the host larvae.

11 Claims, 9 Drawing Sheets

Figure 9:

Ciliates of mosquito larvae
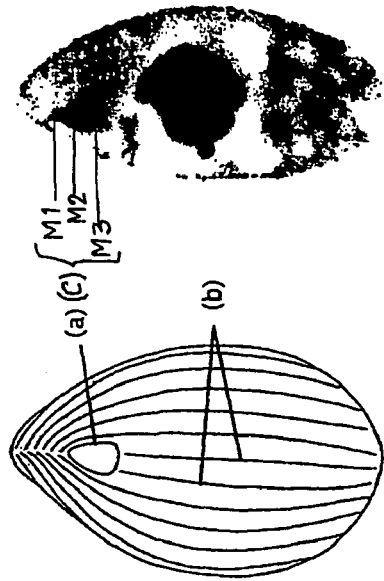
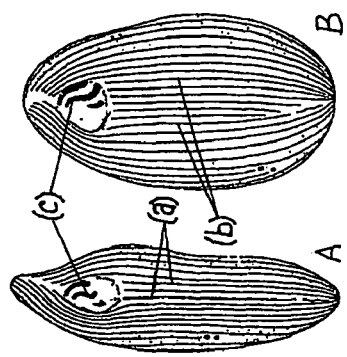
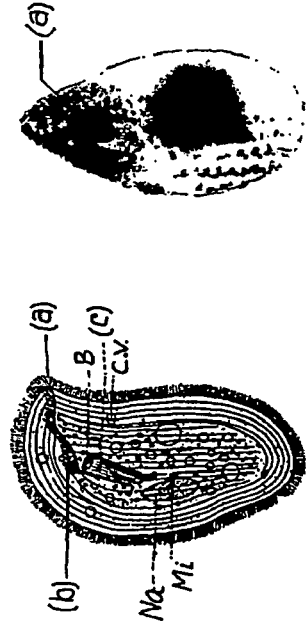
Fig. 1 *Chilodonella*
Fig. 2 *Tetrahymena, Lambornella*
Fig. 3A *Tetrahymena* Fig. 3B
Fig. 4 *Lambornella stegomyiae* A  *L. clarki* B

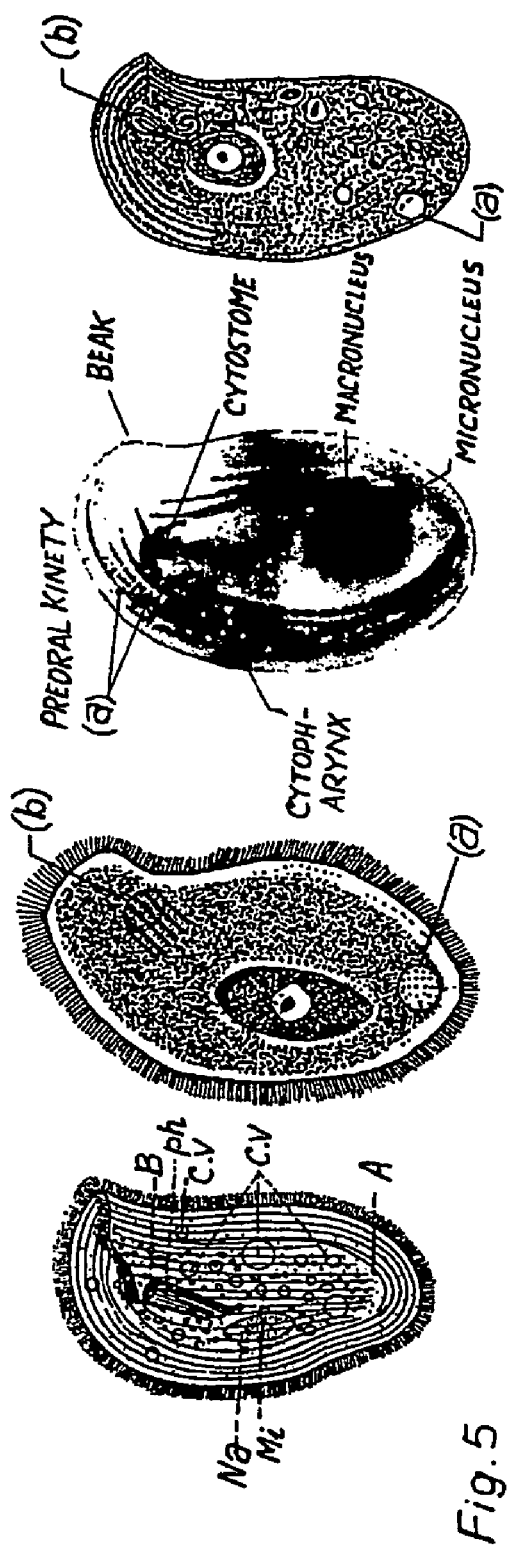

Infected mosquito larva (*Cx. tritaeniorhynchus*) to show endoparasitic ciliate (*Ch. uncinata*) (original magnification 100 X)

Infected mosquito larva (*Cx. tritaeniorhynchus*) with endoparasitic ciliate (*Ch. uncinata*) in situ (original magnification 400 X)

Infected mosuito larva (*Cx. pseudovishnui*) with endoparasitic ciliate (*Ch. uncinata*) ( original magnification 100 X )

Infected mosquito larva (*Cx. pseudovishnui*) with endoparasitic ciliate (*Ch. uncinata*) in situ (original magnification 400 X)

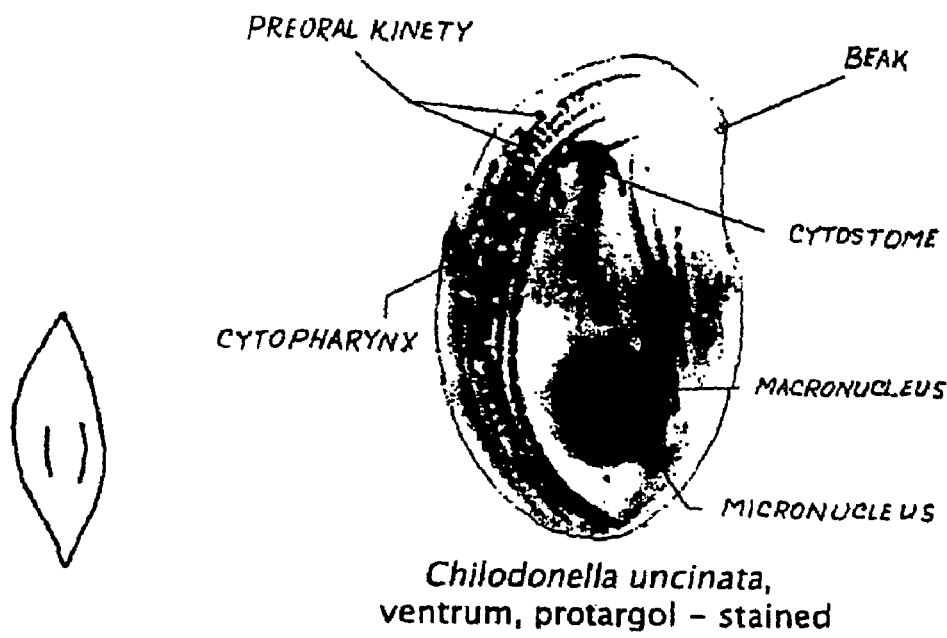
Parasitic Theront form     Free swimming Trophont form
Fig. 14A                    Fig. 14B

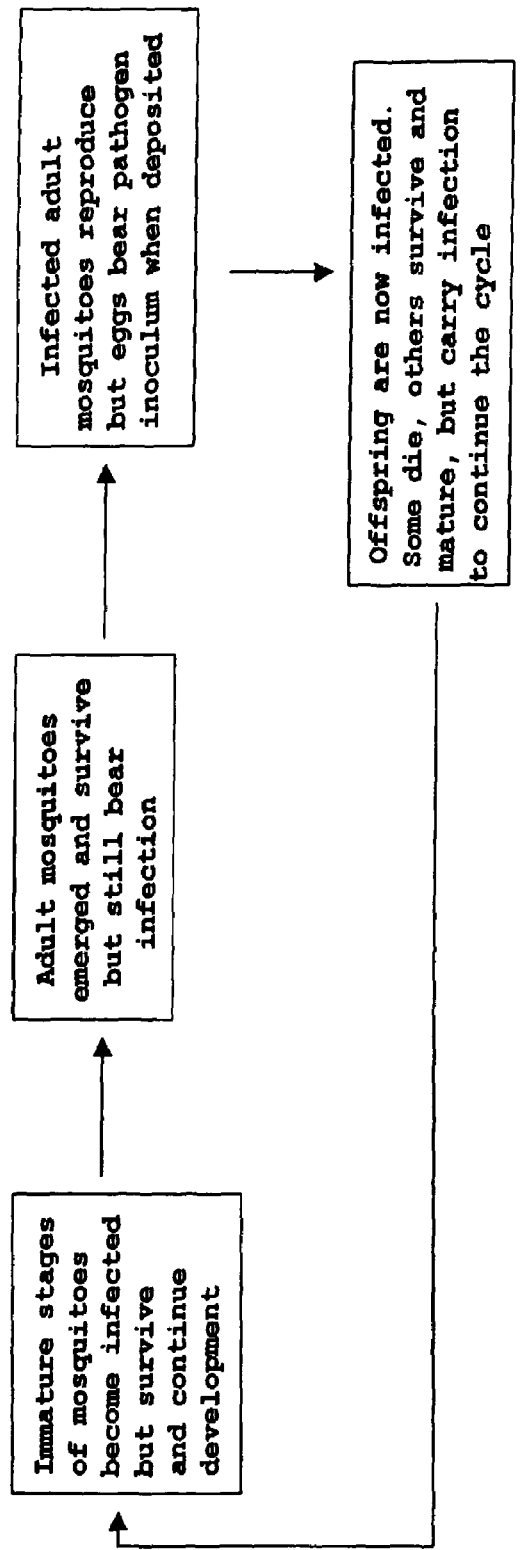
Fig. 15 Persistence of *Chilodonella uncinata*, parasitic ciliate in natural habitat occurs through vertical transmission of these parasites in host mosquito population between two succeeding generations and involves passing the inoculum from reproducing parents to offspring

PROCESS FOR PREPARATION OF A MICROBIAL AGENT

FIELD OF INVENTION

The present invention relates to a process for preparation of a microbial agent containing a ciliated protozoa, *Chilodonella uncinata*, for mosquitoes vectors of human diseases.

PRIOR ART

Over the past half-century, the primary tactics employed to control target mosquito population have involved the use of chemical larvicides and adulticides. Such tactics, although effective when they were initially employed, tend to eventually result in the development of resistance in the target mosquito population, severe suppression of non-target organisms, and/or general pollution of the environment when these tactics are the only ones employed or otherwise overused.

Thus, more biorational approaches are needed to manage mosquito population of public health importance. One such approach would be to combine a chemical insecticide that is highly specific for mosquitoes and otherwise relatively harmless to the environment with one or more biological control agents effective against these insects.

Thus, it is known to use *Bacillus thuringensis* as a microbial agent. However, it has been found that such agents do not propagate in the environment. Thus, it becomes necessary to constantly re-apply the microbial agent, and consequentially raises the end cost of the treatment.

*Coelomomyces* sp. is a fungal pathogen and its efficacy has been evaluated in rice fields for mosquito control. A disadvantage associated with such a microbial agent is that it possesses a complex life cycle and it requires an intermediate host for its continuous reproduction.

Two species of Nematodes, viz. *Romanomermis culicivorax* and *R. iyengari* are known as microbial agents. A disadvantage is that such nematodes require in-vivo production, and are highly sensitive to salinity, organic pollution, temperature extremes and certain agrochemical used in paddy cultivation.

Protozoan pathogens of mosquitoes are ubiquitous and at times produce periodic outbreaks of disease in mosquito larvae those results in severe decline in mosquito population. The microsporidia (Thelohanidae, Nosematidae) and ciliates of the genera *Lambornella* and *Tetrahymena* are some of the most common and best-studied protozoa. Of these, *Lambornella* was found to be highly pathogenic to natural population of tree hole breeding mosquito larvae. A disadvantage of all microsporidians of biological control interest is that it must be grown in living host or host cell culture increasing the cost of producing these agents. Further, the use of insect cell cultures to mass-produce microsporidia is not yet economically feasible because of limitations on the mass culture of insect cell themselves and because the yield of microsporodia spores per infected cell is too low.

OBJECTS OF THE INVENTION

An object of this invention is to propose a process for preparation of a microbial agent containing a ciliated protozoa, *Chilodonella uncinata*, for mosquitoes vectors of human diseases.

Another object of this invention is to propose a process for preparation of a microbial agent containing a ciliated protozoa, *Chilodonella uncinata*, for mosquitoes vectors of human diseases and where the protozoa can easily reproduce.

Still another object of this invention is to propose a process for preparation of a microbial agent containing a ciliated protozoa, *Chilodonella uncinata* for mosquitoes vectors of human diseases which provides a mass killing of mosquito larvae.

Yet another object of this invention is to propose a process for preparation of a microbial agent containing a ciliated protozoa, *Chilodonella uncinata* for mosquitoes vectors of human diseases and wherein the ciliated protozoa is able to naturally recycle itself in various habitats.

A further object of this invention is to propose a process for preparation of a microbial agent containing a ciliated protozoa, *Chilodonella uncinata* for mosquitoes vectors of human diseases and wherein the ciliated protozoa for killing of mosquito larvae need not be repeatedly inoculated.

A still further object of this invention is to propose a process for preparation of a microbial agent containing a ciliated protozoa, *Chilodonella uncinata* for mosquitoes vectors of human diseases wherein the ciliated protozoa which when inoculated can be transmitted from the infected host adult mosquitoes to offspring.

Yet a further object of this invention is to propose a process for preparation of a microbial agent containing a ciliated protozoa, *Chilodonella uncinata* for mosquitoes vectors of human diseases and wherein the ciliated protozoa is robust against all aggressive environs.

BRIEF DESCRIPTIONS OF THE DRAWINGS

Ciliates of Mosquito Larvae

FIG. 1. *Chilodonella*, Ciliates of this genus are dorso-ventrally compressed, with distinct pre-oral beak (a). First time known to be pathogenic to mosquito larvae.

FIG. 2. Genera: *Tetrahymena* and *Lambornella*, body round in transverse section, with no distinct pre-oral beak.

FIG. 3A. *Tetrahymena*, with drop shaped buccal apparatus (a); 2 post oral meridian ciliary rows.

FIG. 3B. Photograph of Tetrahaminid ciliate with all 3 oral polykinid straight (Ml, M2 & M3).

FIG. 4A. *Lamobrnella Stegomyiae*, with 3 post oral meridian ciliary rows (a); only second polykinid sigmoid (c).

FIG. 4B. *Lambomella clarki*, with 7 post oral meridian ciliary rows (b); only second polykinid sigmoid (c).

Indian Species of *Chilodonella*

FIG. 5. *Chilodonella cucullulus*, with contractile vacule numerous & scattered (c.v); cytopharynx lonf & straight (ph).

FIG. 6. *Chilodonella rhesus*, with single contractile vacule (a), cytopharynx short & straight (b).

FIG. 7, *Chilodonella uncinata* (Photograph): contractile vacule 2 in nimber; cytopharynx long and curved (b). (the species first time found to be pathogenic to mosquito larvae).

FIG. 8. *Chilodonella spiralidonds*, contractile vehicle 2 in number, largest posterio-terminal (a); cytopharynx spirally curved (b).

FIG. 9. Photomicrograph of cuticle of dead $2^{nd}$ stage larva (*Cx. tritaeniorhynchus*) showing holes (arrows) through which pathogen (*Ch. uncinata*) entered.

Figure 10:
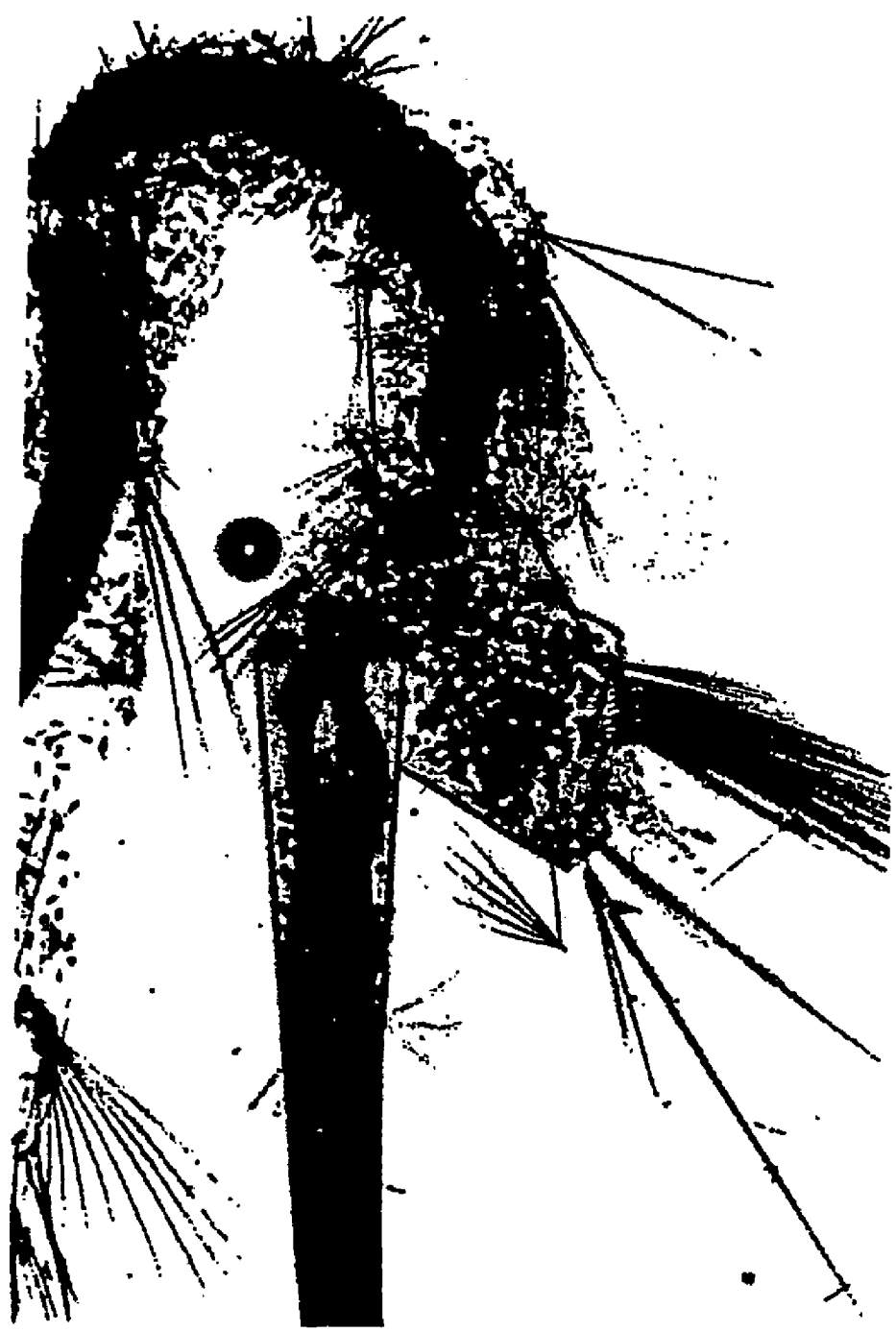

FIG. 10. Photomicrographs of infected and dead $4^{th}$ stage mosquito larva (*Cx. tritaeniorhynchus*), showing (arrows) numerous endoparasitic forms of *Ch. uncinata* at lower magnification.

Figure 11:

FIG. 11. Photomicrographs of same the larva as above at higher magnification (400 ×), showing numerous endoparasitic forms of *Ch. uncinata* (a); degenerating gut visible at (b).

Figure 12:
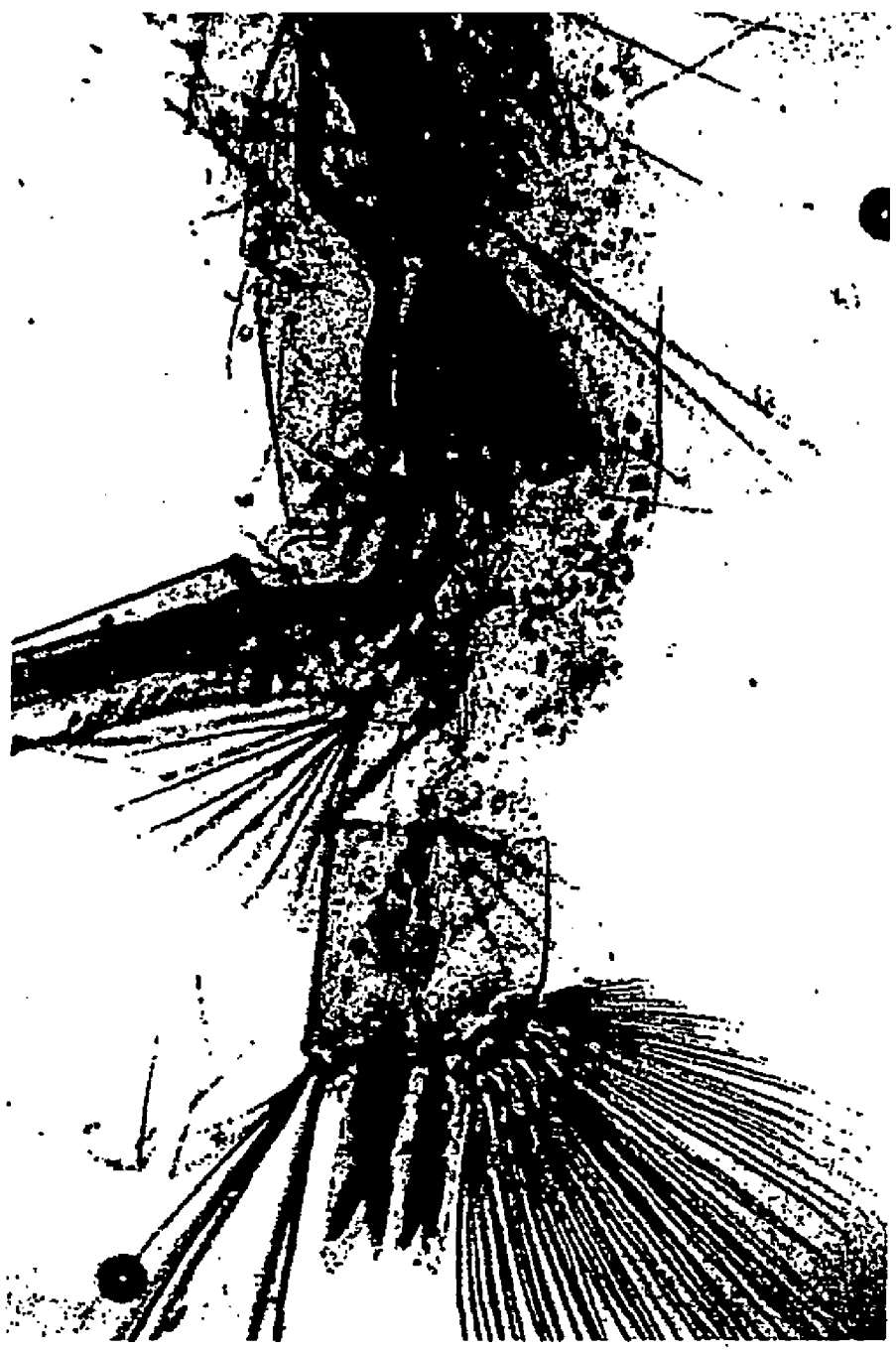

FIG. 12. Photomicrographs of infected and dead 4th stage mosquito larva (*Cx. Pseudovishnui*), showing numerous endoparasitic forms of *Ch. uncinata* (a) at lower magnification; degenerating gut visible at (b).

Figure 13:
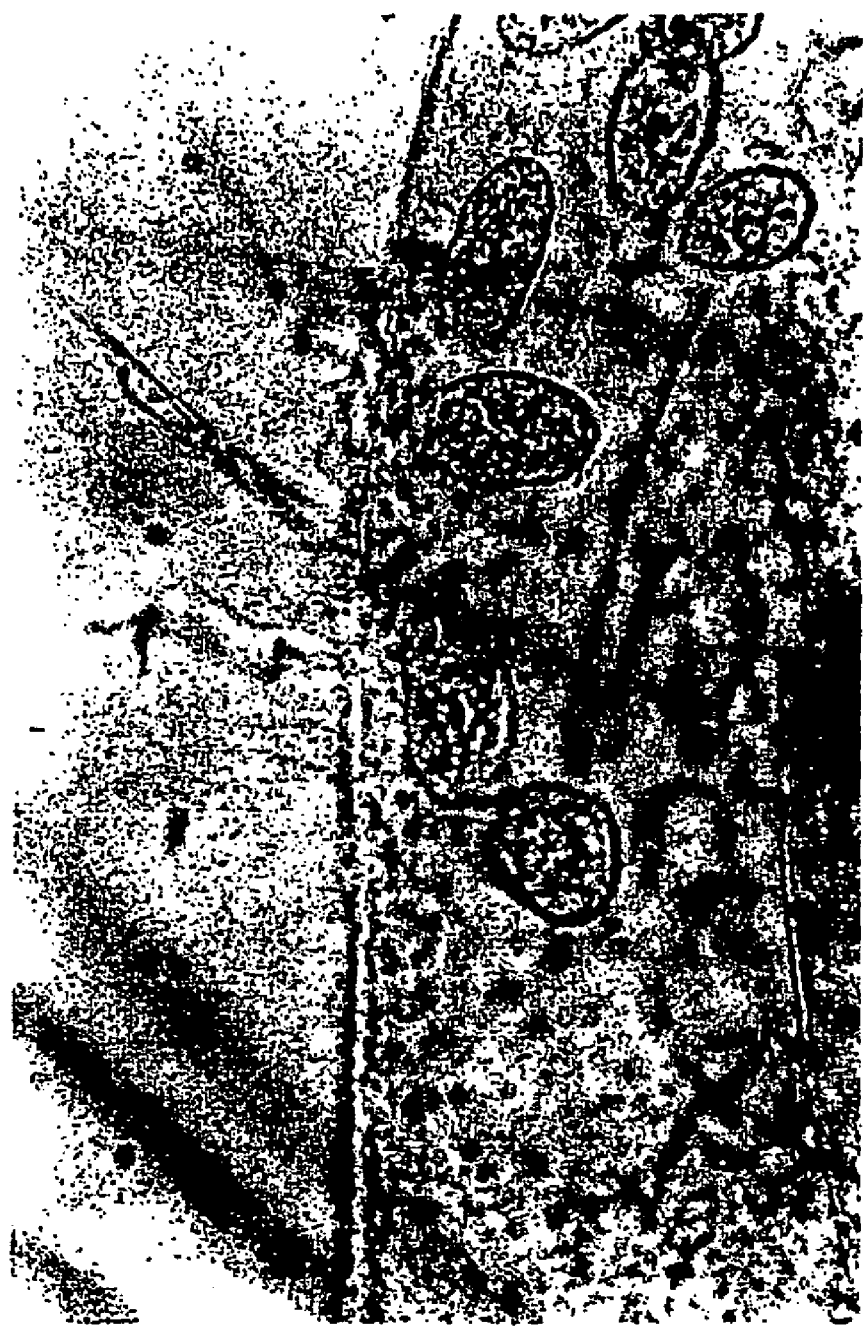

FIG. 13. Photomicrographs of the larva as above at higher magnification (400 ×), showing (arrows) numerous endoparasitic forms of *Ch. uncinata*.

FIG. 14A. *Chilodonella uncinata*, Theront form (parasitic stage), highly motile.

FIG. 14B. *Chilodonella uncinata*, Trophont or Trophozoit form (non parasitic stage). (Identification of the ciliate is based on this stage).

FIG. 15. Natural persistence of *Chilodonella uncinata* between two succeeding generations of host mosquito species (Flow chart shows the way *Ch. uncinata* recycle and disperse in the environment).

DESCRIPTION OF INVENTION

According to this invention there is provided a microbial control agent for mosquito vectors of human diseases comprising a ciliated protozoa, and more particularly *Chilodonella uncinata*, and a carrier such as sand or distilled water and yeast.

Further according to this invention there is provided a method of killing mosquito larvae and particularly the species comprising *Culex tritaeniorhynchus, Cx. pseudovishnui. Cx. (Cx) sp., Cx. (Lutzia) sp.* and *Anopheles hyrcanus* group which comprises in allowing *Chilodonella uncinata* as a ciliated protozoa to be present in said host larvae, allowing the ciliated protozoa to form a hole in the wall of the larvae and to enter into the haemocoelomic cavity of the larvae and to thereby allow the ciliate to feed on the host larvae and simultaneously allowing the host larvae to grow and allow a multiplication of the ciliate, and whereby the multiplied ciliates kill the host larvae.

The composition containing *Chilodonella uncinata* reflected that *Ch. uncinata* in the formulation kills colonized mosquito larvae, viz. *Aedes aegypti, Culex quinquefacitalus* and *Cx. tritaeniorhynchus*. The *Chilodonella uncinata* was found to be highly pathogenic to susceptible host larva. Even a few of them were able to initiate chronic infection. *Ch. uncinata* has following attributes of a promising biological control agent against mosquito larvae particularly vectors of Japanese encephalitis:

Would help mass killing of mosquito larvae

They can be transmitted from the infected host adult mosquitoes to off-springs by virtue of their facility for trans-ovarian transmission They are highly robust against all aggressive environmental condition like temperature, dryness and changes in light intensity etc.

A desirable feature of microbial pathogens is that they are capable of reproduction and have the potential to amplify themselves in the field and cycle through pest population. Thus, the organism must be able to establish an ecological niche against competition from other organisms and must not be unduly sensitive to extremes of temperature, relative humidity or direct sunlight. It should have a high rate of reproduction and be capable of high rate of transmission and infection.

In accordance with the present invention, it has been found that the ciliated protozoa of the present invention has the advantageous properties described herein above.

Reference is now made to Table 1, which reflected that *Ch. uncinata* was detected to be pathogenic to mosquito larvae in nature.

TABLE 1

Type of habitats indicating number of mosquito larvae examined for *Chilodonella uncinata* infection.

| Serial No. | Type of habitat | No. of habitats examined | Larvae examined for infection (number) | | | | | | Species found infected (No.) |
|---|---|---|---|---|---|---|---|---|---|
| | | | 1 | 2 | 3 | 4 | 5 | 6 | |
| 1. | Nursory (Paddy) | 14 | — | — | — | — | 152 | — | 5(16) |
| 2. | Paddy field | 24 | 2703 | 59 | — | — | — | 32 | 1(2174); 2(47); 6(10) |
| 3. | Well water | 5 | 97 | — | 115 | — | — | 3 | 1(86); 3(115) |
| 4. | Irrigation canal | 4 | 121 | — | — | — | — | — | 1(30) |
| 5. | Temporary pond | 32 | 426 | — | — | — | — | — | 1(257) |
| 6. | Burrow pits | 28 | 895 | — | — | — | — | — | 1(751) |
| 7. | Water hyacinth pond | 15 | 156 | — | — | 30 | — | — | 1(45); 4(19) |
| 8. | Marshy area | 2 | 72 | — | — | — | — | — | 1(22) |

1. *Culex tritaeniorhynchus*
2. *Cx. pseudovishnui*
3. *Cx. (Lutzia) sp.*
4. *Cx. (Culex) sp.*
5. *Anopheles stephensi* var. *mysoriensis*
6. *An. hyrcanus* gp.

The findings of small ciliates in the tissues of mosquito larvae indicates infection by at least one of the following: *Chilodonella, Tetrahymena* and *Lambornella*. A brief generic description and a dichotomous key to the species of the genus *Chilodonella* are provided.

Ciliates of Mosquito Larvae

Ciliates belonging to genus *Chilodonella* have Body flat, dorso-ventrally compressed as shown in FIG. 1 with distinct pre oral beak (a), cilia of trophont (free swimming, non parasitic stage) distinct, cover most of ventrum; oral region usually behind pre oral suture (b), cytopharynx usually with well developed rod apparatus (c). In contrast, body of ciliates beloging to other pathogenic genera, viz. *Tetrahymena* and *Lambornella* is round in transverse section (FIGS. 2, 3, 4), uniformly covered with cilia; no distinct pre oral beak; oral region with well developed buccal apparatus (FIGS. 2a, 3Aa).

Key to Indian Species of *Chilodonella*

1. Contractile vacuole numerous, scattered; large size (130–150μ); macronucleus oval; cytopharyns long & straight (FIG. 5)
   *Chilodonella cucullulus*
   Contractile vacuole 1–3 in number
2. Contractile vacuole single (FIG. 6,a); cytopharyns short & straight (6b)
   *Ch. rhesus*
   Contractile vacuole two to three in number.
3. Contractile vacuole two in number; pre-oral kinety complete (FIG. 7,a); cytopharyns short & straight (b); small size (30–50 μm); macronucleus large and round, situated posterio-terminal (c).
   *Ch. uncinata*
   Contractile vacuole two to three in number, largest posterio-terminal (FIG. 8,a); cytopharynx spirally curved behind (b).
   *Ch. spiralidentis*

*Chilodonella uncinata* are small sized ciliates. Body strongly asymetrical, more than twice as long as broad, length 30 μm (mean), width 20 μm. Anterior extremity produced into a beak like projection. Ventral surface flattened, bearing longitudinal ciliary lines only on the anterior half of the body, those on the right half curved and running on to the beak, those on the left half running straight. Dorsal surface convex. Cytostome ventral, situated in the anterior third of the body. Post oral kinety complete. Cytopharynx short & truncate, directed towards the left, with a distinct rod-apparatus. Contractile vacuole two. Macronucleus large (length 8 μm, width 7 μm) & rounded, with a small micronucleus ((2.0–2.5 μm) close to it as in key.

EXAMPLE

A. Problems Encountered In Detection, Isolation, Colonization & Identification of *Ch. uncinata*

Repeated cent percent mortality was observed in mosquito larvae of *Culex tritaeniorhynchus* within 24 hours of collection from paddy fields. However, a lot of difficulty was encountered in recognizing the causative pathogenic microbe due to the following:

1. A few species of lower invertebrates belonging to the genera viz. (Ciliated Protozoa: *Paramecium, Euplotes, Stylonychia*); Thecate *Amoeba* [Phyllum Protozoa] and a species of Rotifer were recorded many-a-times from the same natural habitats of mosquito larvae.
   According to the literature and experts in the field (personal communication) none of these aforesaid microorganisms has been recorded to be pathogenic to mosquito larvae.
2. A species of Vorticella (ciliated Protozoa) was found attached to dead mosquito larvae. Vorticellids are not pathogenic to mosquito larvae. However, under special circumstances, when large number of individuals of Vortecellid get attached to one mosquito larva, with the result due to increased weight the larva is drowned and dead.
3. Dead mosquito larvae collected from paddy fields were washed in distilled water and kept in aliquots for a few days under laboratory condition and observed under microscope. Another dorso-ventrally flattened ciliated protozoa not noticed earlier now appeared in the water containing the dead larvae. In addition, dead larvae were then transparent and some infection as in (FIG. 10) was noted under 100× magnification. At that particular point there was an indication that probably this dorso-ventrally flattened ciliated protozoa (ciliate*) might be the causative microbe killing the mosquito larvae. Contents of those aliquots with contamination of other unwanted and aforesaid ciliates, etc. were discarded. Those containing the candidate (ciliate*) were filtered through 10 μm mesh. These were kept as such for some more days in enamel tray used for colonizing mosquito larvae. To an utter surprise when viewed under the microscope the number of (ciliate*) increased outside the dead mosquito larva and some of them were also found inside the body indicating that these pathogenic microbes were capable of escaping the carcasses of host larva after increasing their number at expense of internal tissues of the host.

To colonize under laboratory condition, available artificial media, viz. Cooked rice, boiled wheat grain, yeast tablet, wheat floor, etc. using glass/plastic beakers and the procedure was standardized. It was found that these (ciliates*) could be produced on mass scale under laboratory condition (Temp. 27±2° C.). Humidity (70–80%) within 48–72 hours using yeast tablet with distilled water as a medium in glass container. Then the medium with the ciliates* is filtered through 10 μm mesh cloth and designated as *Ch. uncinata* (NICD BP-10). The concentration of (ciliate*) was counted using 10 μm of the formulation *Ch. uncinata* (NICD BP-10) on a clean glass slide using a compound microscope in 100× magnification. The concentration is expressed as numbers/ml.

*under study

In the present invention, sterile sand was submerged in the isolate (BP-10) and the sand was allowed to dry at room temperature in the laboratory to get the dry formulation designated as *Chilodonella uncinata* (NICD BP-11). In the dry formulation the pathogen, *Ch. uncinata* remain inactivated.

Batches of infected wild caught mosquito larvae as well as known concentration of the above formulation were kept with colonised mosquito larvae (*Aedes aegypti, Culex quinquifaciatus* and *Anopheles stephensi*) and it was found that infection could be induced in first two species under laboratory condition.

Isolation of ciliate *Ch. uncinata* from adult mosquitoes collected from the study areas in Haryana include keeping 25 female mosquitoes (*Cx. tritaeniorhynchus*) individually in glass specimen tubes with distilled water a procedure followed to raise single female colony. After a gap of 2–5 days, free-swimming form (also known as trophont as in FIG. 14) appeared in the water of 23 specimen tubes. Eggs were laid in 5 specimen tubes. However, in some tubes, eggs failed to hatch while in others larvae died in $2^{nd}/3^{rd}$ instar stage. This indicates the promising capability of this ciliate to get dispersed to newer areas as well as transovarian transmission of *Ch. uncinata* from infected parent to offspring as shown in FIG. 15.

Effect of Desiccation on the Stability of the Formulation *Chilodonella uncinata* (NICD BP-10):

The effect of dryness was evaluated following two simple ways:
i) A number of plastic cups containing *Chilodonella uncinata* (NICD BP-(10) were allowed to dry at room temperature, re-flooded with distilled water after a varying period of time and examined for revival of the pathogen using 10× magnification.
ii) One ml of the isolate *Chilodonella uncinata* (NICD BP-10) was added to 10 gms of sterile sand and was allowed to dry at room temperature. These were submerged in distilled water after a gap of 5, 10, 15, 20, 25 days and examined daily using 10× magnification for the revival of the pathogen.

Results:
i) When re-flooded with distilled water *Ch. uncinata* reappear in the dry plastic cups in a span of 2–5 days time.
ii) Dry and impregnated sterile sand with 1 ml of *Chilodonella uncinata* (NICD BP-10) when submerged in distilled water, *Ch. uncinata* reappear irrespective of prior period of dryness under room temperature.

This shows the ciliate is able to stand desiccation by encysted form and when re-flood excysted into free swimming stage.

This property of the microbial pathogen (*Ch. uncinata*) in the above formulation indicates it is desiccation resistant (robustness) and easy storage of the formulation.

B. *Chilodonella uncinata*: Mode of Entry Inside the Host Body & Subsequent Histopathology The free swimming dorso-ventrally flattened trophont form of *Ch. uncinata* in presence of susceptible mosquito larvae transform into parasitic form (theronts, as in FIG. 14). These parasitic theronts are extremely mobile, very small in size, nearly pointed to club shaped and they seeks 1$^{st}$ and 2$^{nd}$ instar mosquito larva. Then it get itself attached to a convenient site on the body of the larva, form small hole in the cuticle "cuticular invasive cyst" (FIG. 9) and reach the haemocoel of the host larva. On reaching the desired site i.e. (haemocoel) *Ch. uncinata* multiplies and form numerous endoparasitic ciliates/morphs (FIGS. 10, 11, 12 & 13). These ciliates do not usually kill their host at an early stage but let them grow in size so that they also increase their number manifold. Finally when the larva dies these ciliates continue to increase their number for some more time and then transform into numerous trophonts. Moribund and deceased hosts release numerous trophonts, some of which differentiate into theronts that attack surviving predators (mosquito larvae). Those *Ch. uncinata* that cannot effectively penetrate through the host cuticular invasive cyst and make them free of the cuticle are trapped inside the later and are seen as melanized spots on the host larva (as observed in many times on *Aedes aegypti*.

After the above stages were demonstrated it became clear to understand the events that take place in the life history of otherwise free-swimming ciliate *Ch. uncinata* in presence of a susceptible host in the breeding habitat. This type of mode of entry of microbe from outside is known only in two cases namely, *Lambornella* (another ciliated protozoan) and *Coelomomyces* (parasitic fungi) of mosquito larvae. The former breeds in tree holes and parasitises *Aedes sirensis* and the latter require another intermediate host invertebrate in the form of copepodes (Crustaceans) for its production.

Reproduction in *Ch. uncinata* involves nuclear division and the separation of newly formed units. Separation occurs through simple binary fission (which is often noticed in the present study when yeast is added in the rearing medium) and into many daughter cells as endoparasitic ciliates (inside the body of host mosquito larvae).

I claim:

1. A microbial control agent made by the process of:
    isolating *Chilodonella uncinata;*
    colonizing *Chilodonella uncinata* under laboratory conditions using artificial media;
    submerging said *Chiodonella uncinata* in sterile sand;
    allowing the *Chilodonella uncinata* and sterile sand to dry at room temperature;
    thereby producing a dry formulation of *Chilodonella uncinata.*

2. The microbial agent of claim 1, wherein said *Chilodonella uncinata* are isolated from infected larvae and adult mosquitoes.

3. The microbial agent of claim 1, wherein said dry formulation comprises inactive *Chilodonella uncinata*.

4. A method of killing mosquitoes comprising administering the microbial agent of claim 1.

5. The method of claim 4, wherein said microbial control agent is released in distilled water containing mosquito larvae under conditions such that inactive *Chilodonella uncinata* is reconstituted, reconstituted *Chilodonella uncinata* attacks and enters the larvae, and the *Chilodonella uncinata* kills the larvae and escapes the larvae.

6. The method of claim 4, wherein said reconstituted *Chilodonella uncinata* enter the larvae through a cuticle by forming small holes in the cuticle.

7. The method of claim 5, wherein the reconstituted *Chilodonella uncinata* enter the larvae through a haemocoelomic cavity of the larvae.

8. The method of claim 5, wherein said *Chilodonella uncinata* which escapes from the dead larvae is cultivated at room temperature in the presence of artificial nutrition media to produce daughter cells, thereby continuing a cycle of infection.

9. The method of claim 5, wherein said reconstituted *Chilodonella uncinata* remains active for at least two successive generations under lab laboratory conditions and is capable of being dispersed in the environment.

10. A microbial control agent comprising isolated *Chilodonella uncinata* in a dry formulation of sterile sand which when released in water works as an effective biological agent for mosquito vectors of human disease.

11. The agent of claim 9 wherein the human disease is selected from the group consisting of: malaria, filariasis, dengue and Japanese encephalitis.

* * * * *

UNITED STATES PATENT AND TRADEMARK OFFICE
CERTIFICATE OF CORRECTION

| | | |
|---|---|---|
| PATENT NO. | : 7,141,245 B2 | Page 1 of 1 |
| APPLICATION NO. | : 10/468908 | |
| DATED | : November 28, 2006 | |
| INVENTOR(S) | : Das | |

It is certified that error appears in the above-identified patent and that said Letters Patent is hereby corrected as shown below:

Please change the inventor name as follows:
    Title Page, section (75), please change the inventor name from "Bina Pina Das, Delhi (IN)" to -- Bina Pana Das, Delhi (IN)--.

Title Page, section (73), please add the second Assignee as follows:
    --The Secretary, Department of Biotechnology (Secretary)--.

Signed and Sealed this

Twenty-second Day of May, 2007

JON W. DUDAS
*Director of the United States Patent and Trademark Office*

UNITED STATES PATENT AND TRADEMARK OFFICE
CERTIFICATE OF CORRECTION

| | |
|---|---|
| PATENT NO. | : 7,141,245 B2 |
| APPLICATION NO. | : 10/468908 |
| DATED | : November 28, 2006 |
| INVENTOR(S) | : Das |

It is certified that error appears in the above-identified patent and that said Letters Patent is hereby corrected as shown below:

On Title Page

Please change the inventor name as follows:

Item (75), please change the inventor name from "Bina Pana Das, Delhi (IN)" to -- Bina Pani Das, Delhi (IN)--.

Signed and Sealed this

Twenty-first Day of August, 2007

JON W. DUDAS
*Director of the United States Patent and Trademark Office*